United States Patent [19]

Schaefer et al.

[11] Patent Number: 4,873,372

[45] Date of Patent: Oct. 10, 1989

[54] ISOLATION OF 4,4'-DICHLORODIPHENYL SULFONE

[75] Inventors: Gerhard Schaefer, Heidelberg; Heinz Eilingsfeld, Frankenthal; Peter Neumann, Wiesloch; Michael Stumpp, Ludwigshafen, all of Fed. Rep. of Germany

[73] Assignee: BASF Aktiengesellschaft, Ludwigshafen, Fed. Rep. of Germany

[21] Appl. No.: 148,386

[22] Filed: Jan. 25, 1988

[51] Int. Cl.$^4$ .............................................. C07C 147/06
[52] U.S. Cl. ...................................................... 568/34
[58] Field of Search ....................................... 568/33, 34

[56] References Cited

U.S. PATENT DOCUMENTS

| | | | |
|---|---|---|---|
| 3,855,312 | 3/1974 | Horner | 568/34 |
| 4,016,210 | 4/1977 | Horner et al. | 568/34 |
| 4,242,527 | 12/1980 | Mark et al. | 568/34 |

FOREIGN PATENT DOCUMENTS 2555376  6/1977  Fed. Rep. of Germany .
895473   2/1962  United Kingdom .
1572916  5/1980  United Kingdom .

OTHER PUBLICATIONS

M. Farberov et al., English Language Abstract of U.S.S.R. 833,957, May 30, 1981.
Y. Morita et al., Chem. Abstracts vol. 105, No. 60415k (1986).
Tokai Electro–Chemical Co., Chem. Abstracts, vol. 97, No. 127264x (1982).

*Primary Examiner*—Mary E. Ceperley
*Attorney, Agent, or Firm*—John H. Shurtleff

[57] ABSTRACT

A process for the isolation of 4,4'-dichlorodiphenyl sulfone from a mixture of dichlorodiphenyl sulfones in which the ratios of the masses of 2,4'-dichlorodiphenyl sulfone and 3,4'-dichlorodiphenyl sulfone to the mass of 4,4'-dichlorodiphenyl sulfone are respectively from 0.5% to 20% and from 0.5% to 30% by treating the mixture with an alkanol at temperatures of from 20° C. to 250° C., cooling, and separating the pure 4,4'-dichlorodiphenyl sulfone that precipitates.

6 Claims, No Drawings

ISOLATION OF 4,4'-DICHLORODIPHENYL SULFONE 4,4'-Dichlorophenyl sulfone is an important intermediate used mainly for the manufacture of aromatic polysulfones and for the synthesis of bis(4-aminophenyl) sulfone, which is required for the treatment of leprosy and for curing epoxy resins. For these applications 4,4'-dichlorodiphenyl sulfone of high purity is required.

4,4'-Dichlorodiphenyl sulfone can be prepared for instance by the process described in German Patent 1 087 592 by reacting chlorobenzene with a mixture of sulfur trioxide and dimethyl pyrosulfate. German Published Application 2 252 571 describes the preparation from chlorobenzene and chlorobenzenesulfonic acid under elevated pressures at temperatures of from 220° C. to 260° C.

It is also possible to prepare 4,4'-dichlorodiphenyl sulfone by the Friedel-Crafts reaction between 4-chlorobenzenesulfonyl chloride and chlorobenzene in the presence of iron(III) chloride as catalyst, as described in German Patent 2 704 972, for instance. The sulfone synthesis is carried out at about 140° C. with chlorobenzene as solvent.

In all the processes described a mixture of isomeric dichlorodiphenyl sulfones is always obtained, necessitating an additional purification stage to isolate pure 4,4'-dichlorodiphenyl sulfone free from other isomers after the usual separations.

The object of the present invention was to provide a process for the isolation of 4,4'-dichlorodiphenyl sulfone largely free from other isomers from its mixtures with 2,4'- and 3,4'-isomers as they occur in processes such as those mentioned above.

In the novel process that meets this object 4,4'-dichlorodiphenyl sulfone is isolated from a mixture containing dichlorodiphenyl sulfones in which the ratios of the masses of 2,4'-dichlorodiphenyl sulfone and 3,4-dichlorodiphenyl sulfone to the mass of 4,4'-dichlorodiphenyl sulfone are respectively from 0.5% to 20% and from 0.5% to 30% by treating the mixture with an alkanol at temperatures of from 20° C. to 250° C. in such a manner that dissolution is as complete as possible, cooling the resultant mixture to precipitate pure 4,4'-dichlorodiphenyl sulfone, and finally separating the 4,4'-dichlorodiphenyl sulfone in the usual way.

Mixtures from which 4,4'-dichlorodiphenyl sulfone largely free from its isomers can be obtained are, in particular, reaction mixtures given by known processes for the preparation of 4,4'-dichlorodiphenyl sulfone by the reaction of chlorobenzene with sulfonating compounds. In such reaction mixtures the mass fraction of isomeric dichlorodiphenyl sulfones is from 10% to 100%, especially from 40% to 100%, and the other substances that can be present, depending on the process involved, incude methyl hydrogen sulfate, dimethyl sulfate, ethyl hydrogen sulfate, diethyl sulfate, chlorobenzene, iron chloride, sulfuric acid, chlorobenzenesulfonic acid, and chlorobenzenesulfonyl chloride in various amounts.

Examples of suitable alkanols are alkanols with from 1 to 4 carbon atoms. The use of methanol is preferred. The ratio of the mass of alkanol to the mass of 4,4'-dichlorodiphenyl sulfone in the mixture to be treated can be varied within wide limits, for example from 0.1 to 10, but is preferably from 0.5 to 3.

The initial mixture is treated with the alkanol at temperatures of from 20° C. to 250° C. in such a way that it is dissolved as completely as possible. The temperature of the resulting mixture is then lowered to precipitate the pure 4,4'-dichlorodiphenyl sulfone, which is separated in the usual way, for example by filtration.

In particular a reaction mixture given by one of the methods of synthesizing 4,4'-dichlorodiphenyl sulfone mentioned above can, for instance, be run into methanol, while cooling if necessary. If the mixture does not form a solution in the boiling methanol the pressure is raised to increase the boiling temperature. Temperatures of from about 80° C. to 160° C., corresponding to pressures of from about 2 bar to 18 bar, are generally enough.

When alkanols other than methanol are used it may be necessary to cool the reaction mixture before it is run into the alcohol, to avoid reactions such as the formation of olefins. When isobutyl alcohol is used a solution is formed at about 100° C., from which 4,4'-dichlorodiphenyl sulfone at least 99.8% pure precipitates on cooling.

According to German Patent 1 087 592 the reaction mixture resulting from the treatment of chlorobenzene with dimethyl sulfate and sulfur trioxide is diluted with water when the reaction is finished. This precipitates both 4,4'-dichlorobenzene and the unwanted isomers. The dichlorodiphenyl sulfone obtained in this way is not suitable for polymer syntheses since it contains only about 95% of the 4,4'-isomer. Another problem is how to dispose of the considerable amounts of methyl hydrogen sulfate that are formed. These disadvantages are obviated by use of the novel process. The reaction mixture arising from the process described in German Patent 1 087 592 is run into boiling methanol instead of into water. The mixture of dichlorodiphenyl sulfones dissolves when the temperature is raised to about from 105° C. to 115° C. under pressure (from 3.5 bar to 6 bar). The 4,4'-dichlorodiphenyl sulfone that precipitates on cooling and is isolated by filtration is at least 99.8% pure. After it has been dried it can be used for the synthesis of polymers without any further purification.

The novel process makes it possible to recover easily the methyl hydrogen sulfate formed from the dimethyl sulfate used, and recycle it. The alkanol (preferably methanol) is distilled off from the filtrate, under reduced pressure if necessary. The temperature of the residue can then be raised to from 140° C. to 150° C., converting methyl hydrogen sulfate to dimethyl sulfate in the manner known. The dimethyl sulfate can be used again for the synthesis of dichlorodiphenyl sulfone.

Pure 4,4'-dichlorodiphenyl sulfone can be isolated similarly from the reaction mixture that is obtained according to German Published Application 2 252 571 from chlorobenzene and 4-chlorobenzenesulfonic acid. If methanol is used it is not necessary to cool the reaction mixture, whose temperature is over 200° C., and mixing with methanol can take place at the boiling temperature of the latter at atmospheric or elevated pressures. If a $C_2$–$C_4$ alkanol is used it is advisable to reduce the temperature of the reaction mixture to below 100° C. before mixture with the alcohol, in order to avoid formation of olefin by elimination of water. The purity of the 4,4'-dichlorodiphenyl sulfone that is filtered off after cooling and precipitation is at least 99.8%. After removal of the alkanol by distillation—under reduced pressure if necessary—the residue can be returned for use in the synthesis.

The novel process can also be used to particular advantage for the treatment of the reaction mixture that is given by the process described in German Patent 2 704 972. Usually iron chloride is removed from the mixture by washing with water after the addition of chlorobenzene. In the novel process direct treatment of the reaction mixture with the alkanols, after removal of the bulk of the chlorobenzene used as solvent in the synthesis if need be, yields a solution that also contains the iron(III) chloride used as catalyst. The 4,4'-dichlorodiphenyl sulfone obtained by cooling the solution and filtering is at least 99.8% pure. The alcohol and chlorobenzene can be recovered for re-use by rectification of the filtrate. A further advantage of the novel process is the fact that the reaction mixture does not come into contact with water, and the filtrate can be disposed of without ecotoxicological difficulties, with or without previous removal of methanol.

EXAMPLE 1

The reaction mixture obtained by the reaction of 160 g (2 mol) of sulfur trioxide with 225 g (2 mol) of chlorobenzene in the presence of 126 g (1 mol) of dimethyl sulfate in accordance with the example given in German Patent 1 087 592 is stirred into 200 g of methanol at a temperature of 50° C. The mixture is kept boiling under a pressure of 3.5 bar for 1 h, then cooled to 25° C. The precipitated material is isolated and washed three times with 150-g portions of methanol. The dried product weighs 200 g and melts at 149°–150° C. to a water-white liquid. The composition determined by gas chromatography is at least 99.8% 4,4'-dichlorodiphenyl sulfone, not more than 0.1% 2,4'-dichlorodiphenyl sulfone, and not more than 0.1% 3,4'-dichlorodiphenyl sulfone.

The methanol is distilled off from the combined filtrate and washings until the temperature of the liquid reaches 100° C. After removal of methanol the temperature of the liquid is raised to from 140° C. to 150° C. and the dimethyl sulfate formed is distilled under vacuum. In this way 90 g of the dimethyl sulfate employed is recovered.

COMPARATIVE EXAMPLE 1

If the reaction mixture described in Example 1 is treated with water to bring about precipitation a product melting at 138°–142° C. to a brown liquid is obtained. The composition determined by gas chromatography is 95%. 4,4'-dichlorodiphenyl sulfone, 3.5% 2,4'-dichlorodiphenyl sulfone, and 1.5% 3,4'-dichlorodiphenyl sulfone.

EXAMPLE 2

The procedure followed is the same as that described in Example 1, but methanol is replaced by isobutyl alcohol. The mixture is stirred at 100° C. for 1 h, then cooled to room temperature. Isolation of the product as in Example 1 gives 190 g of dried product, which melts at 150° C. to a water-white liquid and whose composition is 99.9% 4,4'-dichlorodiphenyl sulfone and 0.1% 2,4'-dichlorodiphenyl sulfone.

EXAMPLE 3

A mixture obtained by the process described in German Patent 2 704 972 by the reaction of 250 g of 4-chlorobenzenesulfonyl chloride with 200 ml of chlorobenzene in the presence of 10 g of iron(III) chloride at from 150° C. to 160° C. is stirred into 450 ml of methanol, with cooling by boiling. The suspension is boiled under reflux for 2 h, then cooled to 40° C. The precipitate is filtered off, washed four times with 300-ml portions of methanol, and finally dried. The product weighs 290 g and melts at 149° C. The composition determined by gas chromatography is more than 99.7%. 4,4'-dichlorodiphenyl sulfone, less than 0.1% 2,4'-dichlorodiphenyl sulfone, 0.1% 3,4'-dichlorodiphenyl sulfone, and less than 0.1% other compounds.

Fractional distillation of the combined filtrate and washings recovers 1500 ml of methanol and 60 ml of chlorobenzene. The still bottoms are disposed of by incineration.

EXAMPLE 4

A reaction mixture at 220° C., obtained by the process described in German Published Application 2 252 571 and consisting of 560 g of isomeric dichlorodiphenyl sulfones, 210 g of chlorobenzenesulfonic acid, and 10 g of chlorobenzene is stirred into 1000 ml of methanol. The temperature of the mixture is allowed to rise to 100° C., so that the dichlorodiphenyl sulfone that precipitates at first can be seen to redissolve completely. After cooling, filtration, and thorough washing with methanol 380 g of a product melting at 149°–150° C. is obtained. The composition is 99.8% 4,4'-dichlorodiphenyl sulfone, less than 0.1% 2,4'-dichlorodiphenyl sulfone, less than 0.1% 3,4'-dichlorodiphenyl sulfone, and less than 0.1% other compounds.

The residue remaining after the methanol has been distilled off consists mainly of isomeric dichlorodiphenyl sulfones and chlorobenzenesulfonic acid, and can be returned to the reaction vessel.

We claim:

1. A process for the isolation of 4,4'-dichlorodiphenyl sulfone from a substantially water-free mixture containing dichlorodiphenyl sulfones in which the ratios of the masses of 2,4'-dichlorodiphenyl sulfone and 3,4'-dichlorodiphenyl sulfone to the mass of 4,4'-dichlorodiphenyl sulfone are respectively from 0.5% to 20% and from 0.5% to 30%, which process comprises:

treating the mixture with an alkanol at temperatures of from 20° C. to 250° C. under substantially water-free conditions in such a manner that dissolution in the alkanol is as complete as possible, cooling the resultant substantially water-free mixture to precipitate pure 4,4'-dichlorodiphenyl sulfone, and finally separating the 4,4'-dichlorodiphenyl sulfone.

2. A process as claimed in claim 1 wherein an alkanol of from 1 to 4 carbon atoms is employed.

3. A process as claimed in claim 1 wherein the alkanol is methanol.

4. A process as claimed in claim 1 wherein the ratio of the mass of alkanol to the mass of 4,4'-dichlorodiphenyl sulfone in the mixture is from 0.1 to 10.

5. A process as claimed in claim 1 wherein the mixture containing the dichlorodiphenyl sulfones is one obtained by the reaction of chlorobenzene with sulfonating agents.

6. A process as claimed in claim 5 wherein the pure 4,4'-dichlorodiphenyl sulfone is separated by isolating it by filtration, and then distilling off the alkanol from the supernatant liquor which remains and re-using said liquor in a preparation of dichlorodiphenyl sulfone.

* * * * *